(12) United States Patent
Ascione et al.

(10) Patent No.: US 8,674,064 B2
(45) Date of Patent: Mar. 18, 2014

(54) IMMUNOGENIC COMPOSITIONS AGAINST HUMAN PROGASTRIN PEPTIDES

(75) Inventors: Richard Ascione, Jersey City, NJ (US); Shengmei Qi, Jersey City, NJ (US); Bin Wang, Jersey City, NJ (US)

(73) Assignee: Onkologix Ltd, Jersey City, NJ (US)

( * ) Notice: Subject to any disclaimer, the term of this patent is extended or adjusted under 35 U.S.C. 154(b) by 0 days.

(21) Appl. No.: 13/601,106

(22) Filed: Aug. 31, 2012

(65) Prior Publication Data

US 2013/0064841 A1 Mar. 14, 2013

Related U.S. Application Data

(63) Continuation of application No. PCT/US2011/000413, filed on Mar. 3, 2011.

(30) Foreign Application Priority Data

Mar. 3, 2010 (CN) .......................... 2010 1 0116229

(51) Int. Cl.
*A61K 38/00* (2006.01)
*C07K 1/00* (2006.01)
*C07K 14/00* (2006.01)

(52) U.S. Cl.
USPC .......................... 530/324; 530/350; 530/402

(58) Field of Classification Search
None
See application file for complete search history.

(56) References Cited

U.S. PATENT DOCUMENTS

| 546,849 A | 9/1895 | Hughes | |
|---|---|---|---|
| 5,080,896 A * | 1/1992 | Visser et al. | 424/193.1 |
| 5,468,494 A * | 11/1995 | Gevas et al. | 424/195.11 |
| 5,866,128 A | 2/1999 | Gevas et al. | |
| 8,158,128 B2 * | 4/2012 | Grimes | 424/158.1 |
| 2007/0248608 A1 | 10/2007 | Grimes | |

OTHER PUBLICATIONS

Ottewell et al. 2005. Am. J. Physiol Gastrointest. Liver Physiol. 288:G541-9.*
International Search Report dated Nov. 28, 2011, from corresponding International Application No. PCT/US2011/000413.

\* cited by examiner

*Primary Examiner* — Shulamith H Shafer
(74) *Attorney, Agent, or Firm* — Foley & Lardner LLP

(57) ABSTRACT

Immunogens against human extended-progastrin species comprise (A) a mimetic peptide comprised of (i) the amino acid sequence of a progastrin or a N- and/or C-terminal processed species of a progastrin joined to (ii) a 7 amino-acid spacer coupled to (B) an immunogenic carrier. Illustrative of the mimetic peptide/spacer combination are a 21 amino-acid peptide (SEQ ID NO.: 1) and other, related polypeptides (SEQ ID NOs.: 2-5). Pharmaceutical compositions containing such an immunogen display improved immunological properties, including the induction of effective antibody levels shortly after the administration of an initial course of immunogen. Levels of antibody thus elicited stay elevated for several months and readily elevate to higher levels upon subsequent boosting by a single injection of immunogen.

13 Claims, 11 Drawing Sheets

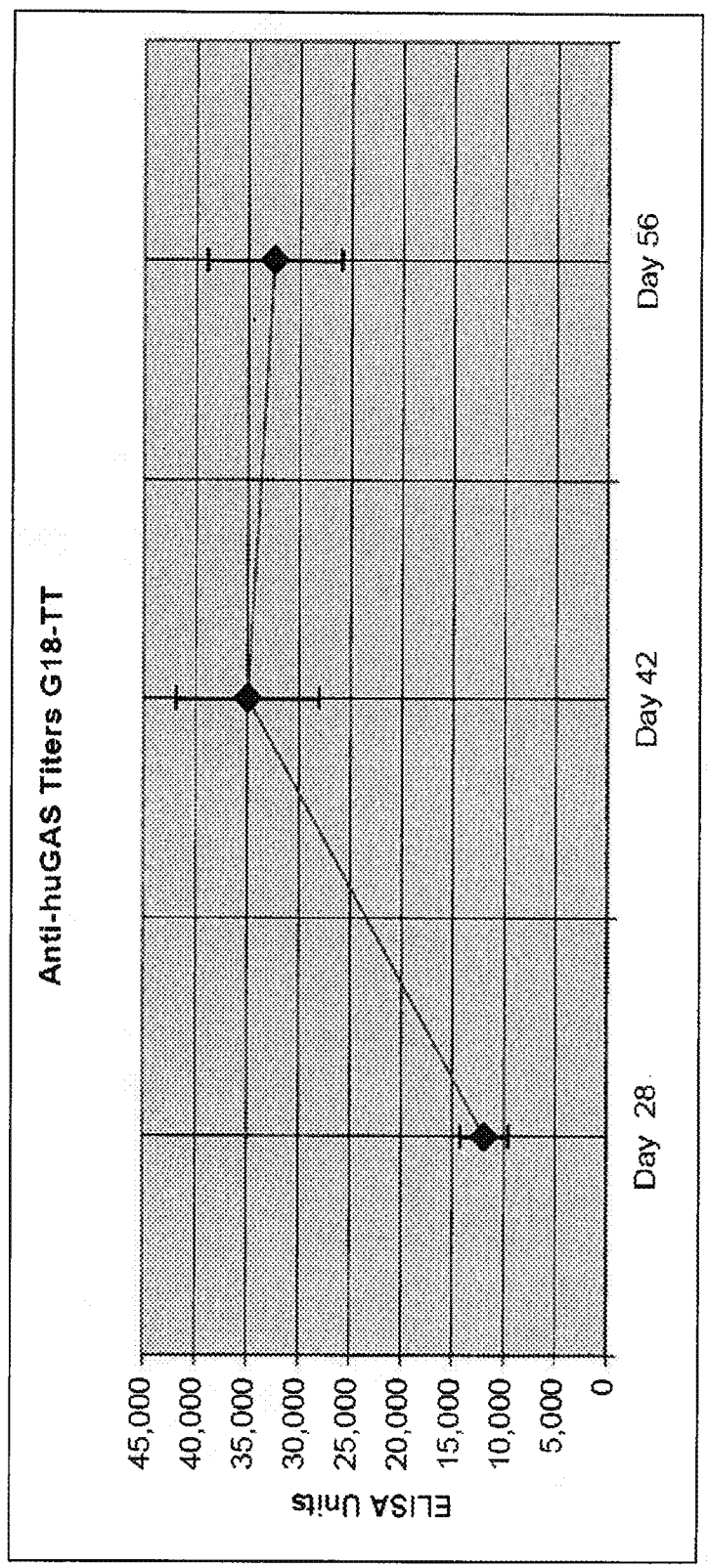
Fig 1A Mouse Anti G18TT ELISA Titers

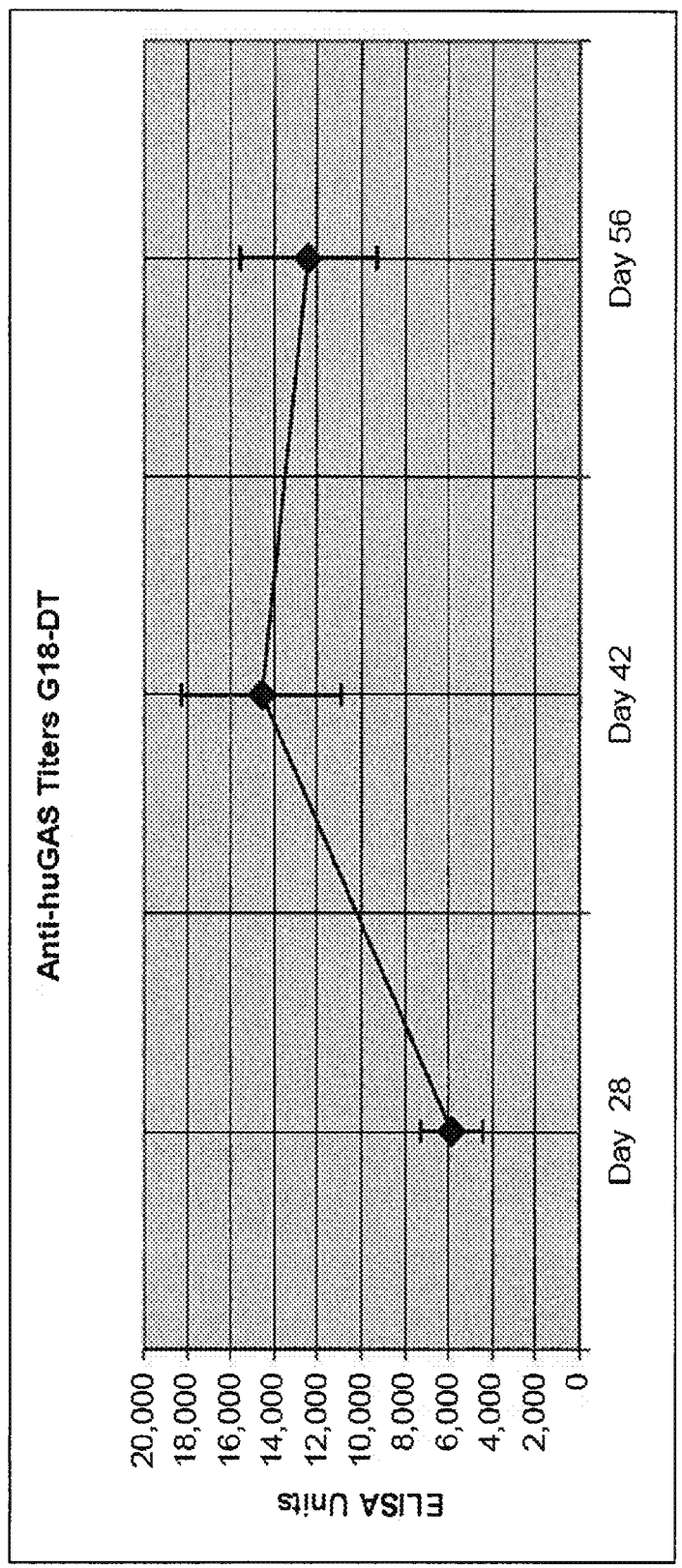
Fig 1B Mouse Anti G18DT ELISA Titers

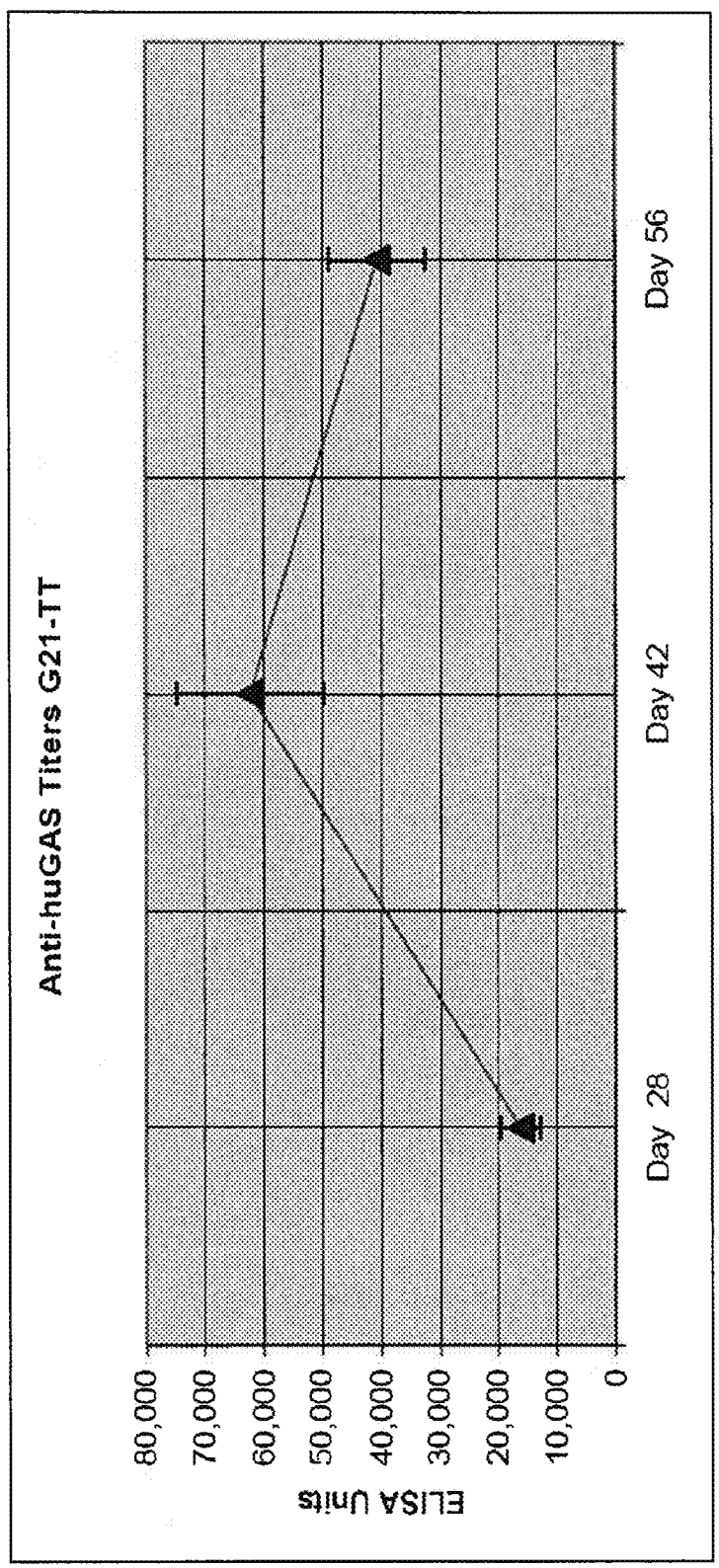
Fig 1C Mouse Anti G21TT ELISA Titers

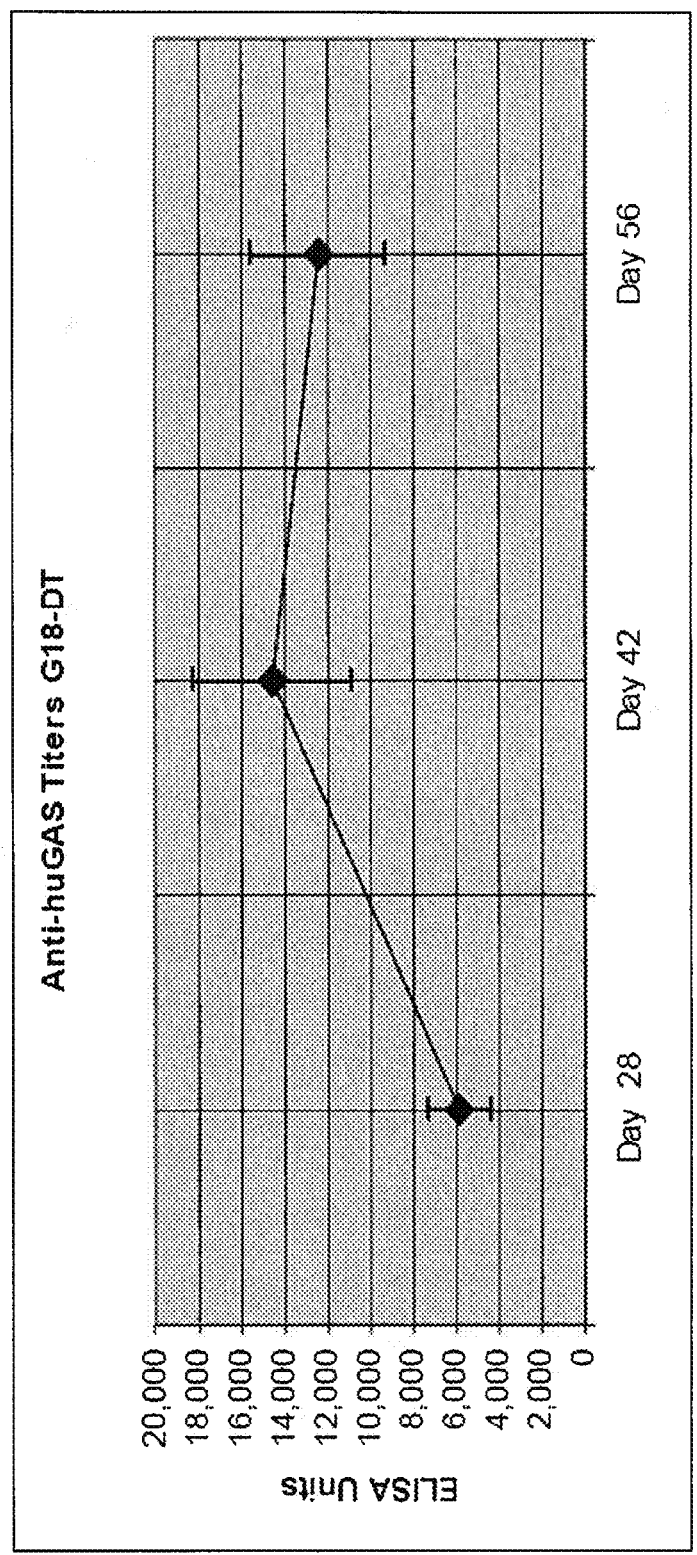
Fig 1D Mouse Anti G21DT ELISA Titers

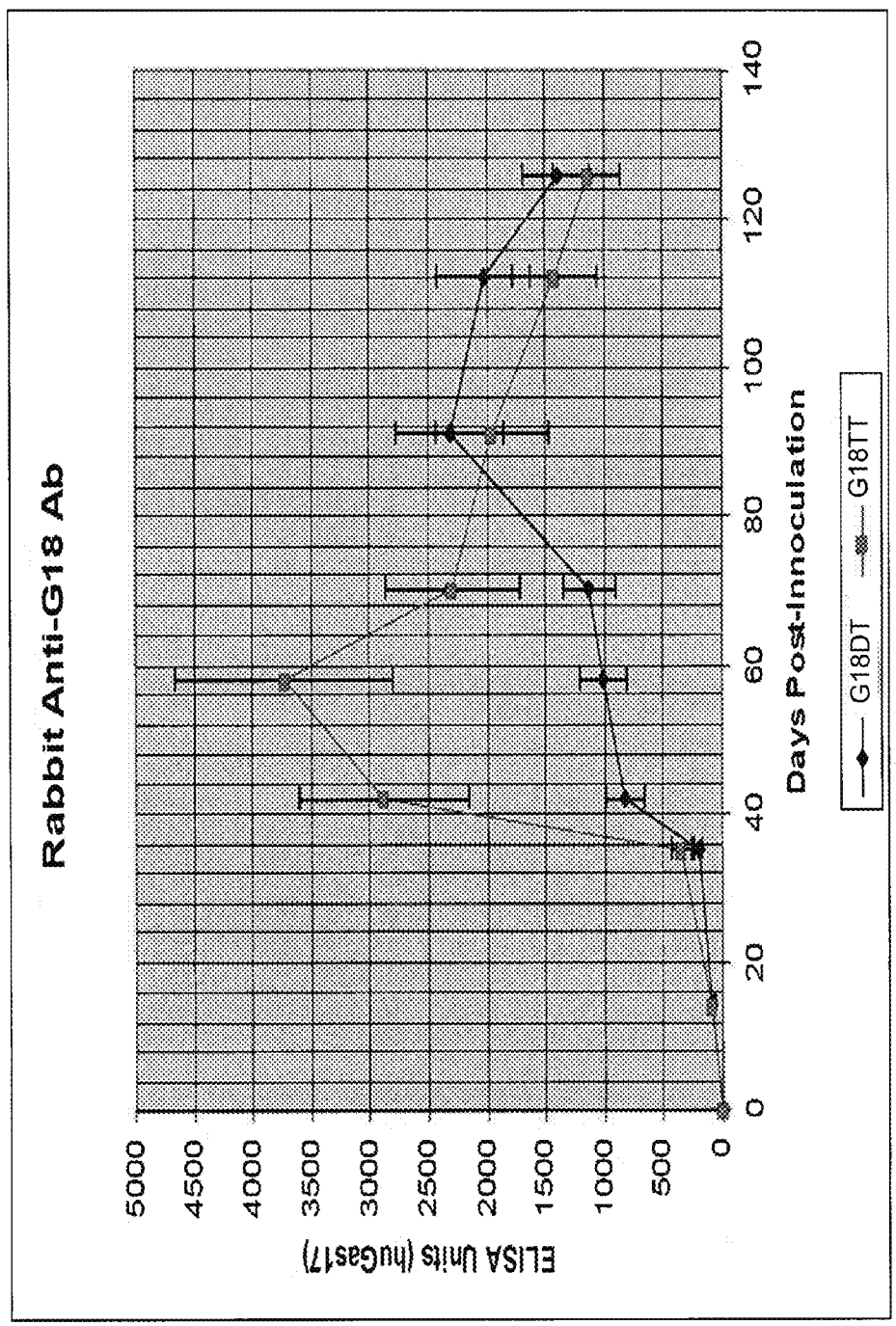
Fig 2 A Rabbit Anti-G18 Titers

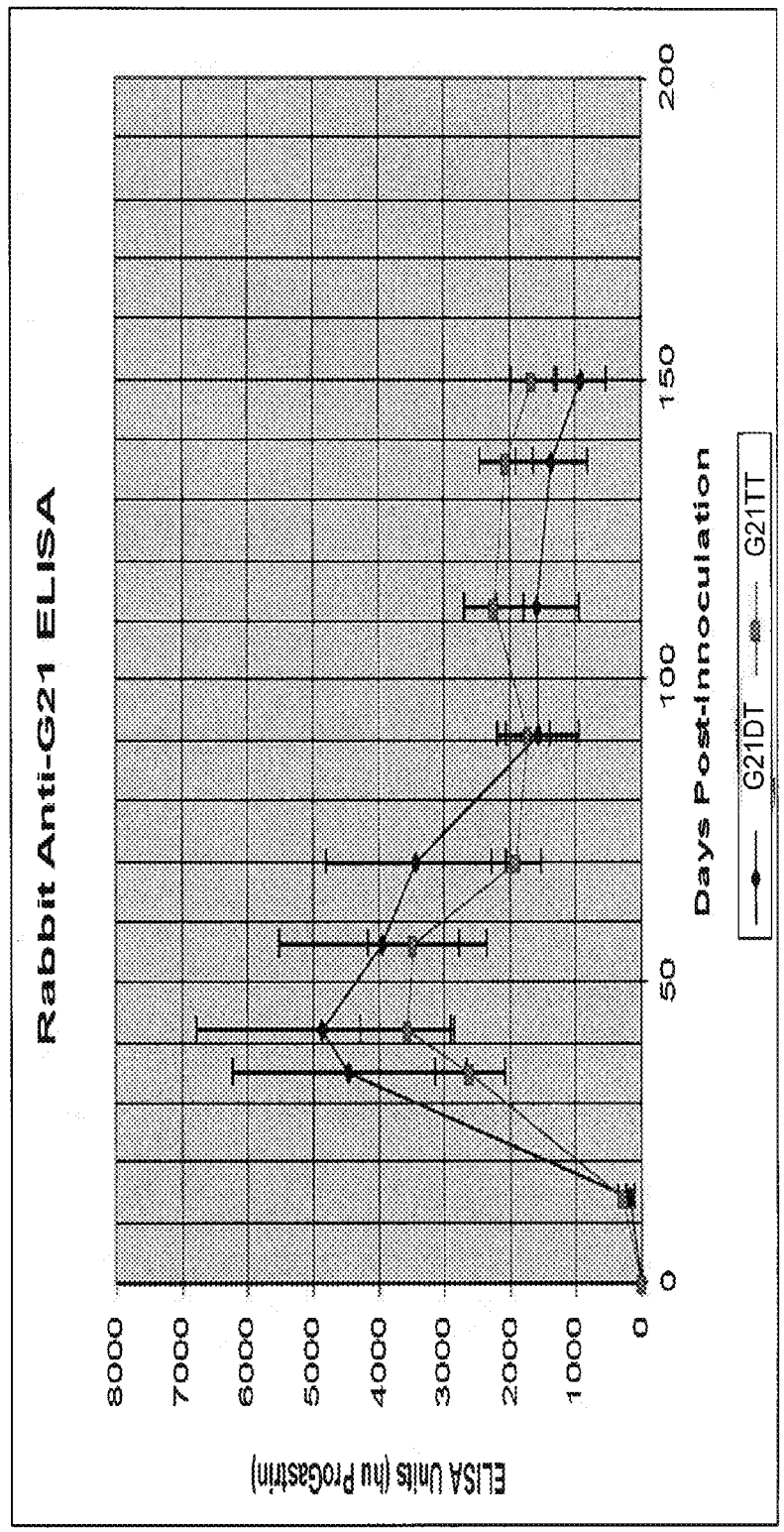
Fig 2B Rabbit Anti-G21 ELISA Titers

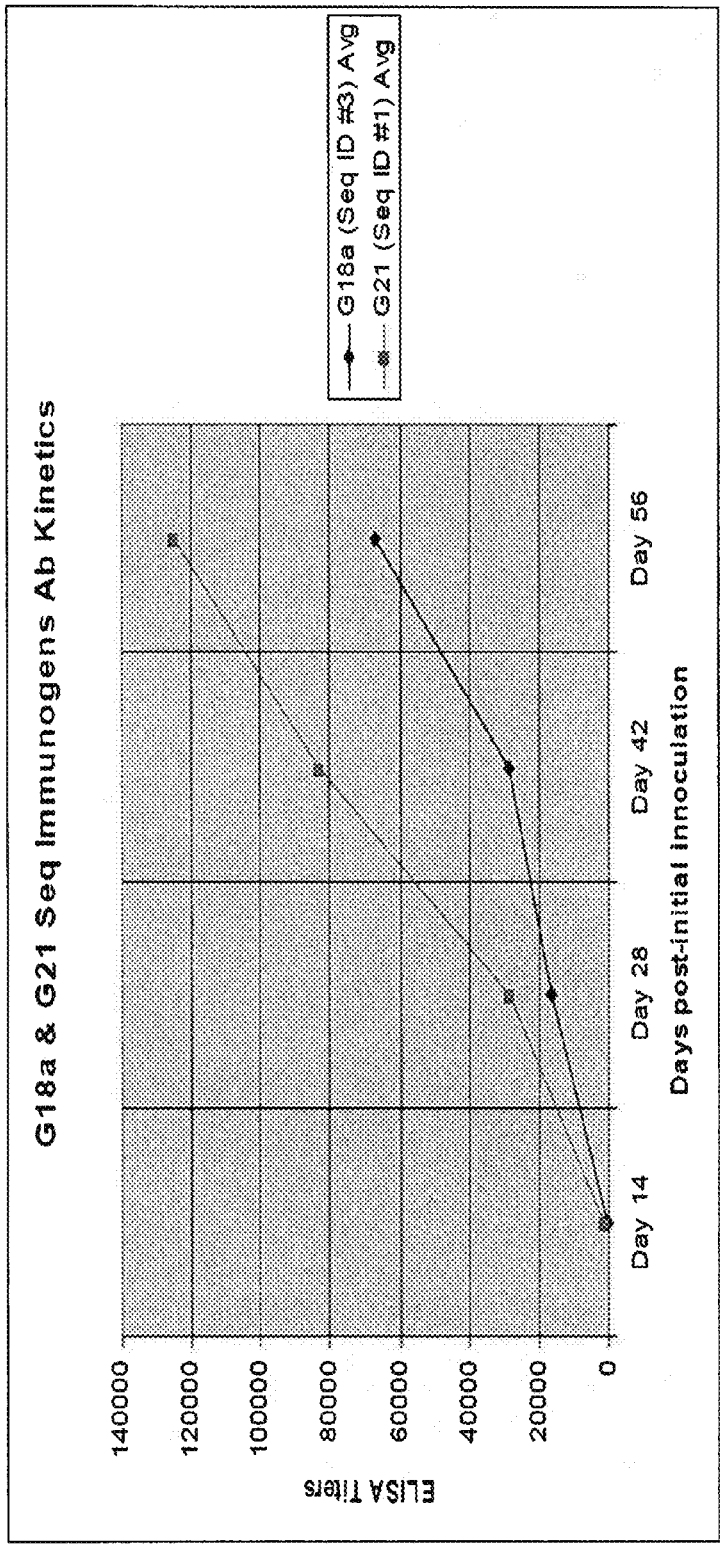

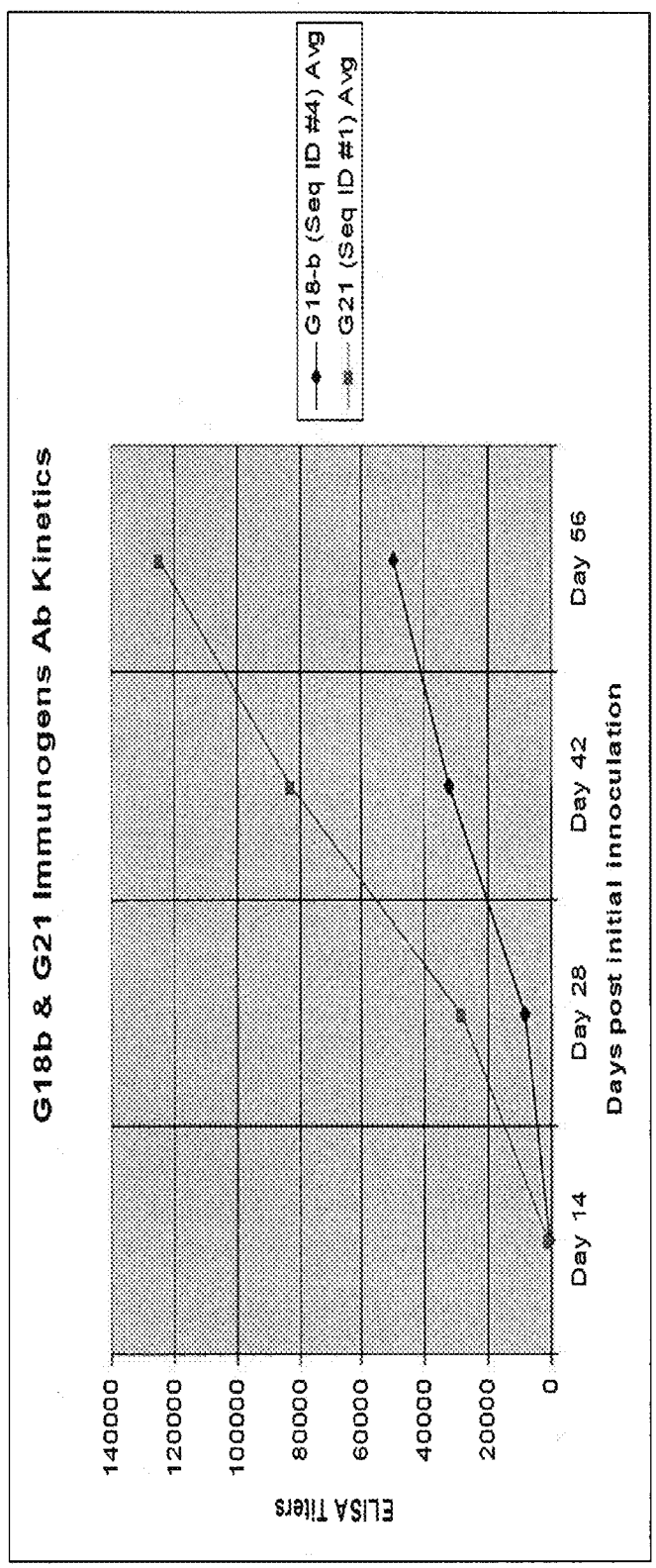
Fig 4B Mouse Anti-human G18-b TT immunogen ELISA titers compared to Mouse Anti-human G21 TT ELISA

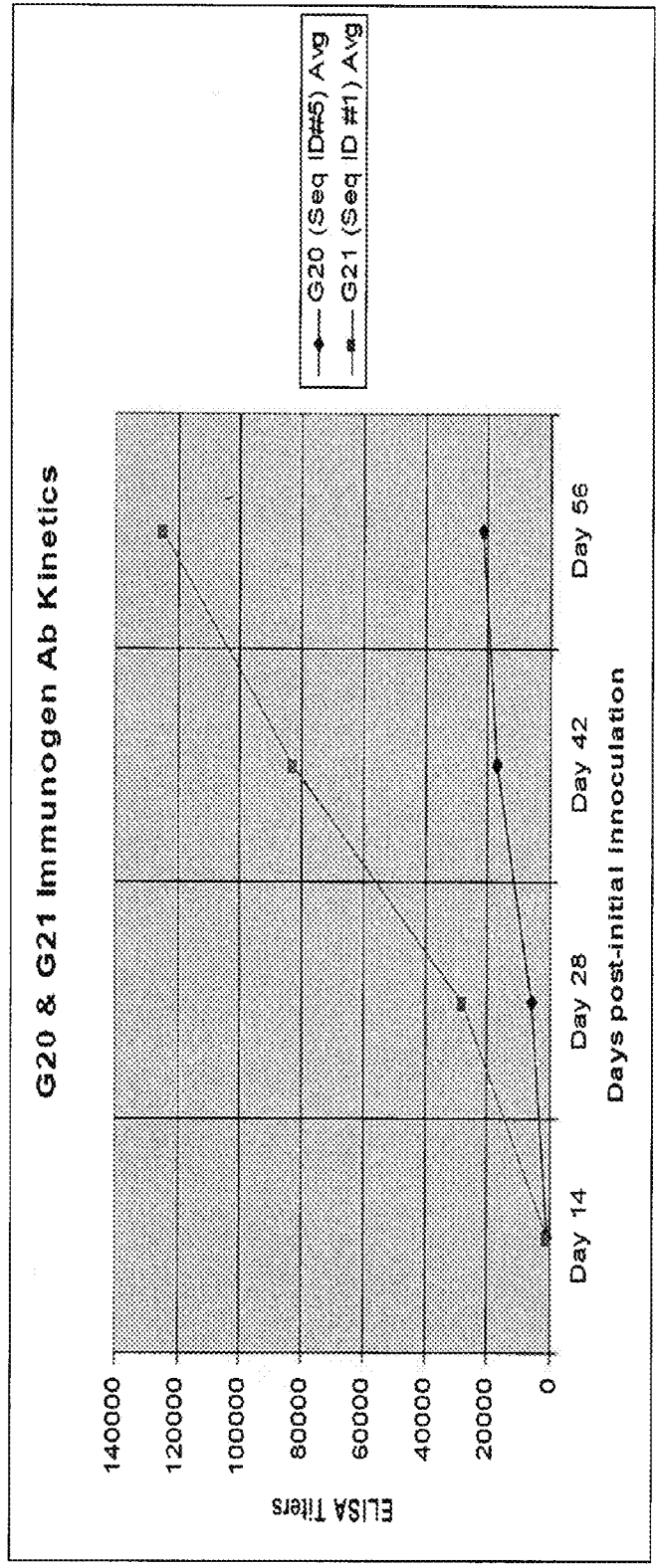
Fig 4C Mouse Anti-human G20 TT immunogen ELISA titers compared to Mouse Anti-human G21 TT ELISA

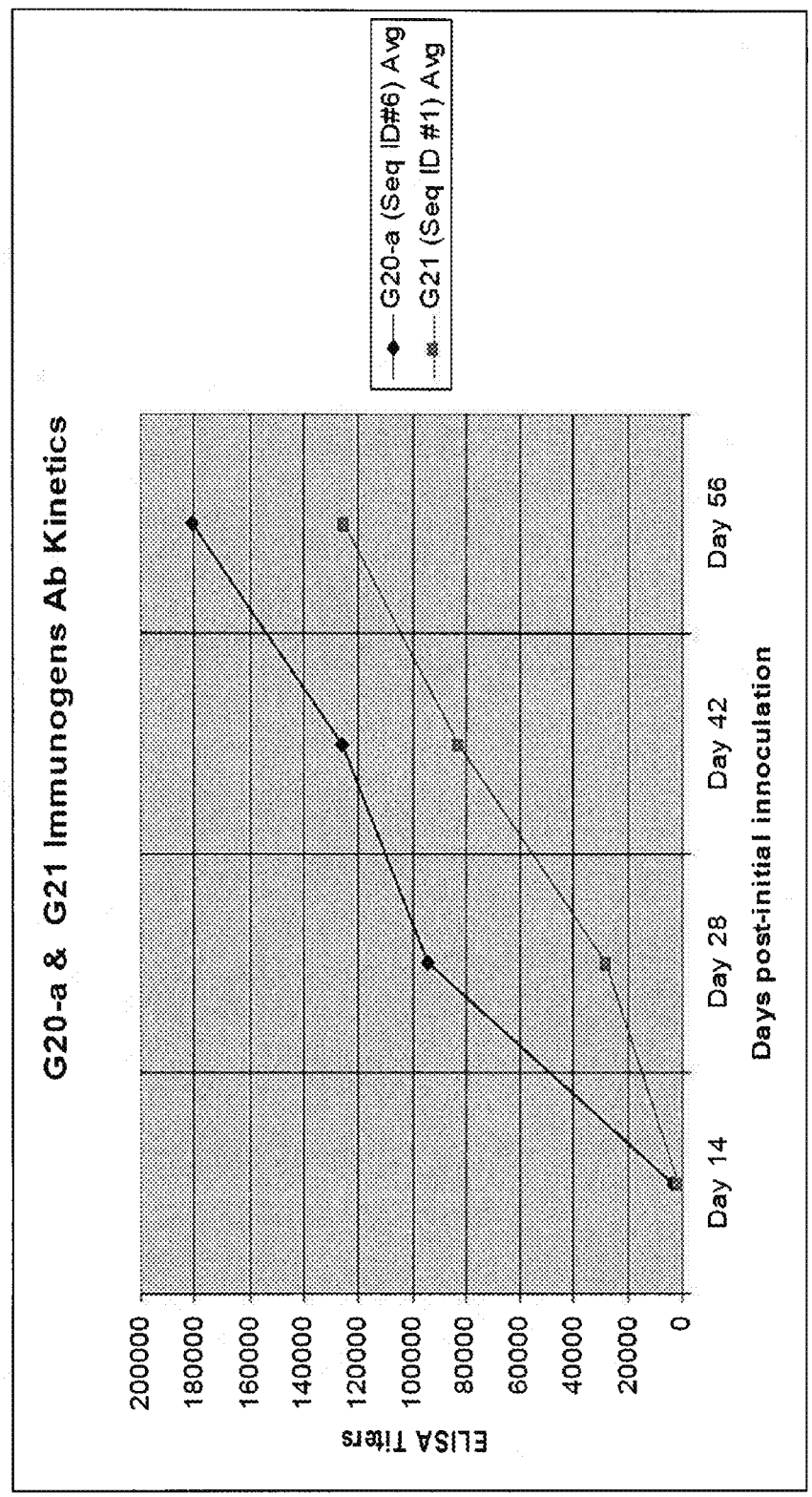
Fig 4D Mouse Anti-human G20-a TT immunogen ELISA titers compared to Mouse Anti-human G21 TT ELISA

IMMUNOGENIC COMPOSITIONS AGAINST HUMAN PROGASTRIN PEPTIDES

CROSS-REFERENCE TO RELATED PATENT APPLICATIONS

This application is a continuation of International Application No. PCT/US2011/000413, filed Mar. 3, 2011, which claims priority to Chinese application number 201010116229.3, filed Mar. 3, 2010. The respective contents of both applications are incorporated herein by reference.

SEQUENCE LISTING

The instant application contains a Sequence Listing which has been submitted in ASCII format via EFS-Web and is hereby incorporated by reference in its entirety. Said ASCII copy, created on Aug. 31, 2012, is named 09958802.txt and is 6,742 bytes in size.

BACKGROUND OF THE INVENTION

Gastrointestinal (GI) cancers are the most common form of cancer in humans worldwide and a leading cause of deaths in most countries. A number of growth factors are known to effect the proliferation of GI malignancies, and particular to them, in common, is the family of peptides hormones generated from the processing of preprogastrin. The maturation of preprogastrin in normal tissue involves the multistep processing of intermediate progastrin, leading to the predominant amidated forms of gastrin found in circulation; gastrin-34 (G34) and gastrin-17 (G17), known, respectively, as "big" and "little" gastrin. These hormones regulate mucosal cell growth and the (post-prandial) secretion of gastric acid, especially following ingestion of food. Progastrin and gastrin, particularly G17 and the glycine-extended form of G17 (gly-G17), have been reported to play a trophic role in GI malignancies, both in vitro and in vivo, and a number of observations support the case for targeted inhibition of these gastrins for therapeutic purposes.

Immunization against specific cancer-promoting growth factors and hormones is known to be useful in the treatment and prevention of certain cancers, especially breast cancer, lung cancer, and certain types of GI cancer. In addition, immunological approaches to the treatment and prevention of gastro-esophageal and gastro-duodenal ulcerating diseases also may be effective in the treatment of these chronic conditions.

Several treatment approaches have been employed successfully, especially ones that use targeted human or humanized monoclonal antibodies (huMAbs). Given the expense and difficulties of setting up manufacture and delivery of commercial huMAbs, however, less expensive alternative strategies are needed, particularly for the developing countries.

For GI cancers and diseases, these immunological approaches entail the generation of specific antibodies to neutralize the biological activity of disease promoting gastrointestinal peptide hormones. The antibodies required have to be specific for a particular growth factor or hormone, or hormone precursor. One or more factors or hormones can be selectively targeted to treat a particular disease.

For instance, human gastrointestinal hormone gastrin 17 ("huG17") is involved in gastrointestinal disease processes including gastro-esophageal reflux disease, by virtue of its ability to stimulate acid and hence cause gastric and duodenal ulceration. Additionally, huG17 has been shown to stimulate the growth of some GI cancers.

Specific anti-huG17 antibodies, which are able to neutralize the action of huG17, therefore have been used in clinical trials to treat diseases in which huG17 is involved. The anti-huG17 antibodies can be administered to the patient, e.g., by passive immunization, or they can be induced in the patient by active immunization.

Similarly, although amidated gastrins were thought to be the only biologically active forms of gastrin in circulation, there now is considerable evidence that the progastrin forms of preprogastrin have proliferative potential based upon studies with human GI cancer patients and derived human cancer cell-lines. In fact, GI cancer cells are generally inefficient at processing gastrin precursors like preprogastrin and progastrin to their normal amidated form; hence, serum levels in cancer patients show much higher levels of these precursor forms of gastrin than for the normal amidated forms. It has been reported that plasma levels of progastrin but not amidated gastrin or glycine extended gastrin are significantly elevated in patients with colorectal cancer compared with those with colorectal polyps or controls (Siddheshwar et al., *Gut* 48: 47-52, 2001). Also progastrin, amidated gastrin, total gastrin, and glycine-extended gastrin were detected in 100%, 69%, 56%, and 44% of colorectal cancer (CRC) patient tumors, respectively (Ciccotosto et al., *Gastroenterology* 109: 1142-53, 1995), suggesting that cancers indeed were faulty in processing gastrins fully.

SUMMARY OF THE INVENTION

To address drawbacks in the conventional technology, as discussed in detail below, the present invention provides, in accordance with one of its aspects, a polypeptide immunogen comprising (A) a mimetic peptide comprised of (i) the amino acid sequence of a progastrin or a species of a progastrin that is N-terminal and/or C-terminal processed, joined to (ii) a 7 amino-acid spacer and (B) an immunogenic carrier coupled to said mimetic peptide. According to one embodiment of the invention, the aforementioned polypeptide immunogen comprises a mimetic peptide that has the amino acid sequence: Cys-pro-Pro-Pro-Pro-Ser-Ser-Gly-Trp-Met-Asp-nPhe-Gly-Arg-Arg-Ser-Ala-Glu-Asp-Glu-Asn (SEQ ID NO.: 1). In accordance with another embodiment, the mimetic peptide has an amino acid sequence that is selected from the group consisting of:

(SEQ ID NO.: 2)
pGlu-Gly-Pro-Trp-β-isoVal-Glu-Glu-Glu-Glu-Ala-Ser-Ser-Pro-Pro-Pro-pro-Cys;

(SEQ ID NO.: 3)
pGlu-Gly-Pro-Trp-Ile-Glu-Glu-Glu-Glu-Ala-Ser-Ser-Pro-Pro-Pro-pro-Cys;

(SEQ ID NO.: 4)
pGlu-Gly-Pro-Trp-Val-Glu-Glu-Glu-Glu-Ala-Ser-Ser-Pro-Pro-Pro-pro-Cys;

-continued

Cys-pro-Pro-Pro-Pro-Trp-Leu-Glu-Glu-Glu-Glu-Ala-Tyr-Gly-Trp-Met-Asp-Phe-Gly; (SEQ ID NO.: 5)
and Cys-pro-Pro-Pro-Pro-Trp-Leu-Glu-Glu-Glu-Glu-Ala-nPhe-Gly-Trp-Met-Asp-Phe-Gly. (SEQ ID NO.: 6)

Pursuant to the invention, the immunogenic carrier can be selected from, among others, tetanus toxoid, diphtheria toxoid, pertussin toxoid, and tuberculin pure protein derivative.

In accordance with another aspect of the present invention, an immunogenic composition is provided that comprises an effective amount of a polypeptide immunogen, as described above, and a pharmaceutically acceptable vehicle for the immunogen. In a preferred embodiment, the pharmaceutically acceptable carrier comprises an emulsion of an aqueous phase, in which the immunogen is present, and an oily phase. The oily phase comprises at least one biodegradable oil, such as squalene, squalane, sorbitan monooleate, Polysorbate 40, and/or Polysorbate 80. The oily phase also may comprise a separate emulsifier. In addition, either the oily phase or the aqueous phase may contain one or more adjuvants.

In accordance with yet another aspect, the invention provides a 7 amino-acid spacer peptide that is especially suitable in joiner with a mimetic peptide, as described above. Illustrative of such spacer peptide is one having an amino acid sequence selected from the group consisting of: Ser-Ser-Pro-Pro-Pro-pro-Cys (SEQ ID NO.: 7); Ser-Ser-pro-pro-pro-pro-Cys (SEQ ID NO.: 8); Thr-Thr-Pro-Pro-Pro-pro-Cys (SEQ ID NO.: 9); and Thr-Thr-pro-pro-pro-pro-Cys (SEQ ID NO.: 10).

BRIEF DESCRIPTION OF THE FIGURES

FIG. 1 depicts antibody responses in mice as measured by ELISA and are in response to three immunizations with immunogens comprising each of the conjugates hG18-TT, hG18-DT, hG21-TT and hG21-DT (A, B, C and D, respectively).

FIG. 2 depicts antibody responses in rabbits, as measured by ELISA, with one administration of a conjugate constructed with peptide 1 (hG18-TT) and peptide 2 (hG21-TT) of Examples 1 and Example 2 below, per A and B, respectively.

FIG. 4 depicts results obtained by immunizing mice with different immunogen conjugates of the invention (A through D, respectively), compared to results obtained with the G21 immunogen.

DETAILED DESCRIPTION OF THE INVENTION

Figure 3:
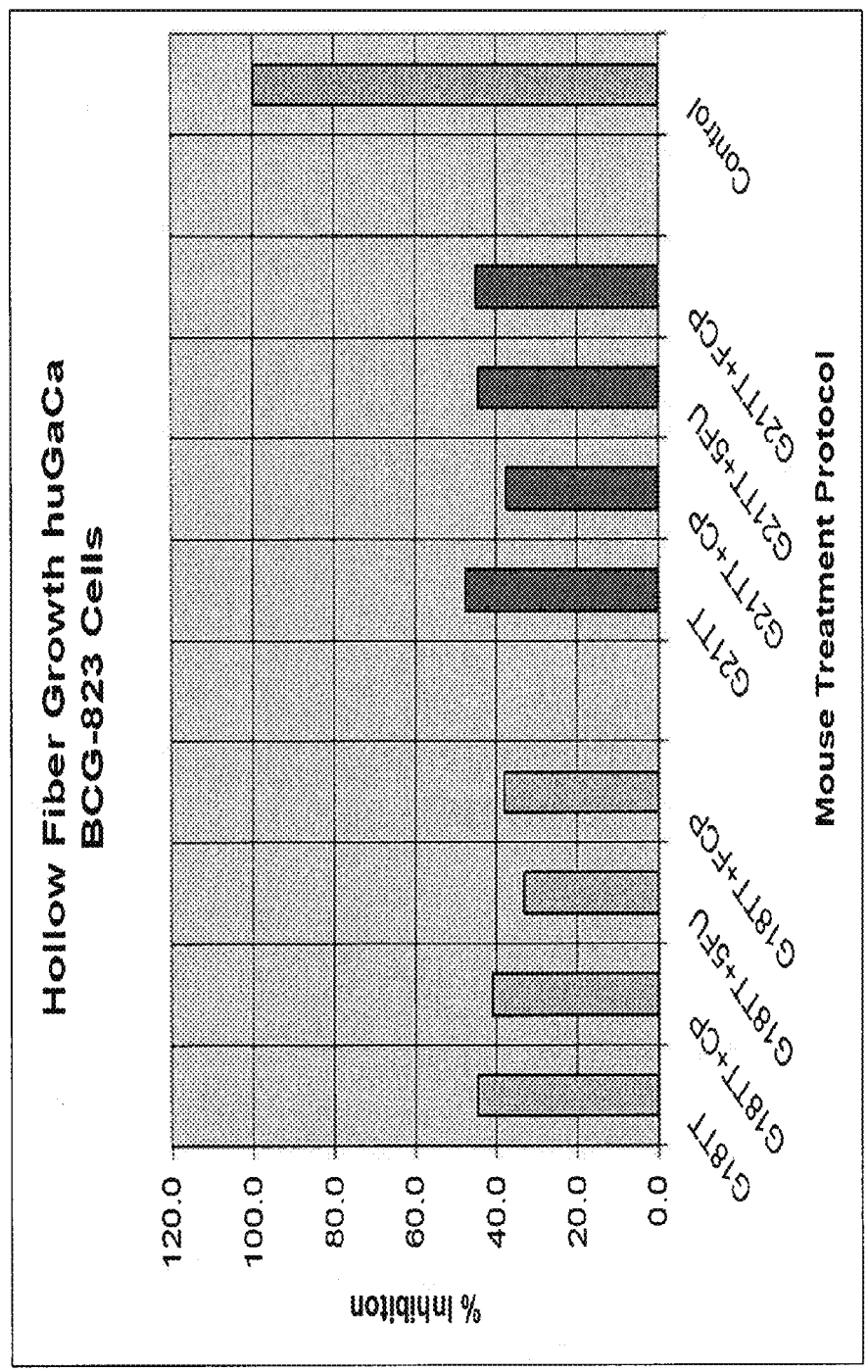
FIG. 3 depicts inhibition of human gastric cancer cells (BCG-823 Cells) in mice treated with immunogens G18-TT and G21-TT. Day 42 animals were implanted with sterile, sealed, hollow fiber tubules containing the human gastric cancer cells. As indicated, some animals received convention gastric cancer chemotherapeutic drugs in addition to the immunogens.

Active immunization against growth factors or gastrointestinal peptide hormones is accomplished by administering to the patient an immunogen that contains chemical structures that induce antibodies binding to the targeted factor or hormone. Such chemical structures are constructed as an immunological peptide mimic of the targeted factor or hormone, and they can be composed of any molecule that immunologically cross-reacts with the target or epitope of that target. These immunogens are immunological peptide mimics ("immunomimics") that may possess the inherent capacity to induce antibodies, e.g., they may be immunogenic. Yet immunomimics often are not inherently immunogenic and therefore must be linked to a carrier with a strong immunogenic property (an "immunogenic carrier"), thereby to render the complex immunogenic.

Pursuant to the present invention, any chemical structure can serve as the immunomimic that immunologically cross-reacts with an epitope of huG17 as illustrated, for example, by Watson et al., *Expert Opin. Biol.* 1: 309-17 (2001), and Watson et al., *Cancer Res.* 56: 880-85 (1996). In a preferred embodiment of the invention, a peptide mimetic is a portion of huG17 that contains within it the amino terminal epitope of huG17, which is designed to stimulate a cross-reactive antibody that will bind to human small gastrin as well as to glycine-extended gastrins. The spacer element of the immunogen serves as a linkage point through which the immunomimic (peptide mimetic plus spacer) is attached to the carrier. The spacer also can affect the immune response against the epitope portion of the immunogen.

Immunizations using an N-terminal nonapeptide portion of huG17 coupled via a spacer to diphtheria toxoid have been reported to inhibit both experimental ulcers in rats and GI human cancer xenografts in immunocompromised mice. A number of clinical trials using this immunogen, known as "G17DT," in patients with GI cancer were performed with significant results, see Watson et al. (2001), but the latest U.S. phase III clinical trial with this immunogen failed to reach statistical significance in the treatment of late-stage pancreatic cancer.

Although showing some successes in early clinical trials, the G17DT approach did not take into account of the marked heterogeneity of gastrin gene expression, particular in GI malignant diseases. In normal gastric cells and tissue, the most abundant secreted/circulating gastrin species are G17 and G34. Numerous scientific reports show, however, that these latter species in fact may constitute less than 50% and, in certain cases, as little as 10%-20% of the gastrin forms in circulation.

The majority species are processed intermediates, known as "progastrins," which are described, for example, in Rehfeld et al., *Regulatory Peptides* 120: 177-83 (2004). Progastrins have been shown to have substantial growth promoting activities that are independent of the traditional gastrin receptors. Thus, the antibodies raised by the G17DT immunogen, mentioned above, likely would capture only G17 and C-terminally extended forms but not the major circulating species of unprocessed/partly processed forms of gastrin (progastrins), abundant in the circulation of GI cancer patients.

It is this disadvantage, among others in the conventional technology, that the novel immunogen compositions of the present invention address by targeting forms of gastrin and progastrins found in circulation in cancer patients. In this regard, the present inventors discovered that certain peptide mimetics of huG17, when coupled to a suitable spacer peptide, yield immunogens that result in an unexpectedly improved immune response, compared to conventional immunogens.

The inventors also discovered that, pursuant to the invention, modified amino acids can be used to enhance the "foreign" intrinsic property of the adjacent peptides, even while permitting the eliciting of cross-reactive antibodies, often at greater levels than the peptide containing the native, natural amino acid. More specifically, it is known that processing by macrophages and monocytes of invading microorganisms and "foreign" antigens results in halogenations reactions and oxidation and nitrosylation reactions. The resultant chemical modifications thus were understood to augment antigenicity and subsequent immunogenicity of proteins and peptides. Accordingly, the present invention encompasses the inclusion of one or more halogenated or nitrosylated amino acid residues, such as para-chloro or para-nitrophenylalanine residues, in order to augment the immunogenicity of a peptide immunogen. This is the reason, for instance, that para-NO$_2$-phenylalanine (nPhe) appears in certain of the inventive immunogens (SEQ ID NOs: 1 and 6) detailed below.

According to one aspect of the invention, therefore, an improved immunogen generates polyclonal antibodies against progastrins and N-terminal and/or C-terminal processed species of progastrins, respectively. Illustrative of such immunogens is one that comprises (i) a peptide of the amino acid residues: Cys-pro-Pro-Pro-Pro-Ser-Ser-Gly-Trp-Met-Asp-nPhe-Gly-Arg-Arg-Ser-Ala-Glu-Asp-Glu-Asn (SEQ ID NO: 1) coupled to (ii) an immunogenic carrier. (See below for conventions applied in the listing of sequences in the present description.) Accordingly, this embodiment incorporates a progastrin component (residues 88-101 of preprogastrin) plus a 7 amino-acid spacer to constitute an immunomimic that is a 21 amino-acid (G21) peptide.

In the present context, the immunogenic carrier can be any suitable, high molecular-weight carrier, typically a protein or large (i.e., generally greater than 6000 kD) molecule of sufficient molecular complexity that can engender an immune response for a haptene or peptide sequence that is covalently linked to it. The category of suitable immunogenic carriers is exemplified by but not limited to diphtheria toxoid (DT), tetanus toxoid (TT), pertussin toxoid, and tuberculin pure protein derivative (PPD). Among these, tetanus toxoid is a preferred immunogenic carrier. The category also encompasses particulate carriers such as the nano-heads described by Fifis et al., *J. Immunol.* 173: 3148-54 (2004), and commercially available dendrimers, e.g., PAMAM dendrimers and MAP dendrimers. See Aguilar et al., *J. Pept. Sci.* 15: 78-88 (2009).

In the present context, the phrase "pharmaceutically acceptable vehicle" denotes a medically safe, non-toxic substance that will convey an immunogen without diminishment of its immunogenic effect. A suitable vehicle can be a liquid emulsion, as further described below, or it can be a stable particulate substance, e.g., as a pharmaceutically safe lyophilized powder or pharmaceutically acceptable silica gel or synthetic, non-infectious virus like particle (VLP). See FIELDS VIROLOGY, Vol. 1, D. M. Knipe & P. Howley (eds.), Lippincott Williams & Wilkins (2007).

For this invention, a preferred form of pharmaceutically acceptable vehicle is an emulsion of an aqueous phase, containing the polypeptide immunogen, and an oily phase. The oily phase comprises at least one biodegradable oil, immiscible with the aqueous phase, that is non-toxic in the dosage range of intended administration. The oil can be natural or synthetic, and there are a variety of such oils available that are generally recognized as meeting international regulatory norms for therapeutic use. Illustrative of such suitable oils are squalene, squalane, sorbitan monooleate, Polysorbate 40, and Polysorbate 80. A preferred oily phase comprises all five of these oils.

In addition, the oily phase may contain a separate emulsifier, such as aluminum monostearate or an adjuvant-active saccharide oleate or saccharide stearate ester.

In accordance with another aspect of the invention, either the oily or aqueous phase of an emulsion as described above contains at least one adjuvant that is distinct from the immunogenic carrier component of the polypeptide immunogen. There is a wide range of known adjuvants, any one or more which may be considered for use in this invention. Illustrative of such known adjuvants are Nor-MDP, Imiquimod, cyclic diguanylate, threonyl-N-acetyl-muramyl-L-alanyl-D-isoglutamine, Isoprinosine, trehalose dimycolate, QS-21, alpha-galactosylceramide (α-GalCer), and alphaglucosylceramide (α-GluCer). For this adjuvant role, moreover, the present invention comprehends the use of a material that, if not typically deemed an adjuvant per se, is immunostimulatory nevertheless. Exemplary of these materials are Ergamisol, Cimetidine, Praziquantel, uric acid, mannan and derivatives of mannan, and vitamin E.

In accordance with a further aspect of the invention, an improved immunogen generates polyclonal antibodies against the amino terminal epitope of huG17 and gly-huG17. Illustrative of these immunogens is one that comprises (i) a peptide of the sequence: pGlu-Gly-Pro-Trp-isoVal-Glu-Glu-Glu-Glu-Glu-Ala-Ser-Ser-Pro-Pro-Pro-pro-Cys (SEQ ID NO: 11) coupled to (ii) an immunogenic carrier, as described above. Here as elsewhere in this description, "isoVal" denotes a beta amino acid mimic of Leu, which may be substituted for Leu generally, and "pGlu" is pyroglutamate, an amino acid derivative that is found at the bioactive N-terminus of the huG17 hormone. Again, tetanus toxoid is the preferred immunogenic carrier for this embodiment, where a modification of the N-terminal huG17 (residues 76-86 of preprogastrin) plus a 7 amino-acid spacer constitutes an immunomimic that is a G-18 peptide.

A further embodiment of the invention is an immunomimic that comprises (i) a peptide of the sequence pGlu-Gly-Pro-Trp-Val-Glu-Glu-Glu-Glu-Glu-Ala-Thr-Thr-Pro-Pro-Pro-pro-Cys (SEQ ID NO.: 12) coupled to (ii) an immunogenic carrier, as described above. Tetanus toxoid likewise is the preferred immunogenic carrier in this embodiment, in which a modification of N-terminal huG17 (modified residues 76-86 of preprogastrin) plus a 7 amino-acid spacer constitutes a G-18 LV peptide, an immunomimic of huG17. As an alternative, according to this embodiment, a peptide of the sequence pGlu-Gly-Pro-Trp-Ile-Glu-Glu-Glu-Glu-Glu-Ala-Ser-Ser-Pro-Pro-Pro-pro-Cys (SEQ ID NO: 3), designated "G18 LI," is used as peptide (i) in constituting a homologous immunomimic of huG17.

Still another embodiment of the invention is an immunomimic comprising (i) a peptide of the sequence: Cys-pro-Pro-Pro-Pro-Trp-Leu-Glu-Glu-Glu-Glu-Glu-Ala-Tyr-Gly-Trp-Met-Asp-Phe-Gly (SEQ ID NO.: 5) coupled to (ii) an immunogenic carrier, as described above. Thus, this embodiment is a glycine-extended immunomimic of huG17, in which residues 79-93 of preprogastrin plus a 7 amino-acid spacer constitute a G-20 peptide.

Also an embodiment of the invention is an immunomimic that comprises (i) a peptide of the sequence: Cys-pro-Pro-Pro-Pro-Trp-Leu-Glu-Glu-Glu-Glu-Glu-Ala-nPhe-Gly-Trp-Met-Asp-Phe-Gly (SEQ ID NO.: 6) coupled to (ii) an immunogenic carrier, as described above. Accordingly, this embodiment is a modified glycine-extended immunomimic of huG17 in which residues 79-93 of preprogastrin plus a 7 amino-acid spacer constitute a G-20 YF peptide.

The remainder of the peptide sequences listed below (SEQ ID NOs.: 7-10) are spacers that contain one or more D-isomer prolyl amino acids, a feature that the present inventors discovered is important for proper positional presentation of adjacent immunogen peptides onto the carrier. In this context, the D-amino acid isomer enables appropriate configuration as well as enhances the persistence of the immunogen for APC presentation, yielding higher titers of antibody.

In the listing below the peptide identified as SEQ ID NO.: 7 is the spacer peptide Ser-Ser-Pro-Pro-Pro-pro-Cys. Furthermore, SEQ ID NO.: 8 is the spacer peptide Ser-Ser-pro-pro-pro-pro-Cys, SEQ ID NO.:9 is the spacer peptide Thr-Thr-Pro-Pro-Pro-pro-Cys, and SEQ ID NO.: 10 is the spacer peptide Thr-Thr-pro-pro-pro-pro-Cys.

In conventional technology, the induction of effective antibody responses by immunization with immunomimic-carrier complexes typically requires two or more administrations of immunogen, and it takes several weeks or months for the antibody titers to rise to the desired levels. By contrast, the improved immunogens of the present invention induce effective levels of antibody shortly after the administration of initial course of immunogen. Levels of antibody thus elicited stay elevated for several months and readily elevate to higher levels upon subsequent boosting by a single injection of immunogen.

The present invention is described further by reference to the following examples, which are illustrative only and not limiting of the invention.

Example 1

Peptides were prepared by standard solid state synthesis methods. Each peptide was characterized as to amino acid content and purity.

Peptides with the amino acid sequences listed below were thus synthesized. In these sequences, as in others of the present description, an amino acid beginning in a capital letter is an L-isomer amino acid, while one beginning in a lower case letter is a D-isomer.

(1) Cys-pro-Pro-Pro-Pro-Ser-Ser-Gly-Trp-Met-Asp-nPhe-Gly-Arg-Arg-Ser-Ala-Glu-Asp-Glu-Asn (SEQ ID NO.: 1), designated "G-21"

(2) pGlu-Gly-Pro-Trp-isoVal-Glu-Glu-Glu-Glu-Glu-Ala-Ser-Ser-Pro-Pro-Pro-pro-Cys (SEQ ID NO.: 11), designated "G-18"

(3) pGlu-Gly-Pro-Trp-isoVal-Glu-Glu-Glu-Glu-Glu-Ala-Ser-Ser-Pro-Pro-Pro-pro-Cys (SEQ ID NO.: 11), designated "G-18 LV" (human G17 homologue)

(4) pGlu-Gly-Pro-Trp-Ile-Glu-Glu-Glu-Glu-Glu-Ala-Ser-Ser-Pro-Pro-Pro-pro-Cys (SEQ ID NO.: 3), designated "G18 LI"

(5) Cys-pro-Pro-Pro-Pro-Trp-Leu-Glu-Glu-Glu-Glu-Glu-Ala-Tyr-Gly-Trp-Met-Asp-Phe-Gly (SEQ ID No.: 5), designated "G-20"

(6) Cys-pro-Pro-Pro-Pro-Trp-Leu-Glu-Glu-Glu-Glu-Glu-Ala-nPhe-Gly-Trp-Met-Asp-Phe-Gly (SEQ ID No.: 6), designated "G-20"

(7) Ser-Ser-Pro-Pro-Pro-pro-Cys (SEQ ID NO.: 7), a Seryl-Prolyl spacer that is a 7 amino-acid peptide (8) Ser-Ser-pro-pro-pro-pro-Cys (SEQ ID NO.: 8), a Seryl-all D-Prolyl spacer that is a 7 amino-acid peptide (9) Thr-Thr-Pro-Pro-Pro-pro-Cys (SEQ ID NO.: 9), a Threonyl-Prolyl spacer that is a 7 amino-acid peptide

(10) Thr-Thr-pro-pro-pro-pro-Cys (SEQ ID NO.: 10), a Threonyl-all D-Prolylspacer that is a 7 amino-acid peptide Peptide 1 (SEQ ID NO.: 1) contains a para-nitrophenylalanine-modified amino terminal immunomimic of progastrin (-Gly-Trp-Met-Asp-nPhe-Gly-Arg-Arg-Ser-Ala-Glu-Asp-Glu-Asn) (SEQ ID NO: 13), preceded by the carboxy terminal spacer -Ser-Ser-Pro-Pro-Pro-pro-Cys (SEQ ID NO.: 7) attached to the preprogastrin residue N-terminal side of 88-101. Peptide 2 (SEQ ID NO.: 2) comprises an 11 amino-acid immunomimic of huG17 (pGlu-Gly-Pro-Trp-Leu-isoVal-Glu-Glu-Glu-Glu-Ala-(SEQ ID NO: 14), a homologue of huG17 with isoVal substituted for Leu, followed by the spacer -Ser-Ser-Pro-Pro-Pro-D-Pro-Cys (SEQ ID NO.: 7) attached to the amino acid number 86 of preprogastrin residue of the huG17 immunomimic, Peptide 3 (SEQ ID NO.: 3) comprises the 11 amino acid immunomimic homologue, -Ser-Ser-pro-pro-pro-pro-Cys; (SEQ ID NO.: 8), which is the same as in Peptide 2 except that Val is substituted for isoVal, attached to the amino acid number 86 of preprogastrin residue as described above. Peptide 4 (SEQ ID NO.: 4) comprises the 11 amino-acid immunomimic of huG17, pGlu-Gly-Pro-Trp-Ile-Glu-Glu-Glu-Glu-Glu-Ala-Tyr-Gly-Trp-Met-Asp-Phe-Gly (SEQ ID NO: 15), likewise as in Peptide 2 except that Ile is substituted for isoVal, followed by the spacer -Ser-Ser-Pro-Pro-Pro-pro-Cys (SEQ ID NO.: 7) attached to preprogastrin C-terminal of residue number 79, of the immunomimic of huG17. Peptide 5 (SEQ ID NO.: 5) comprises the 15 amino-acid immunomimic of gly-huG17. Trp-Ile-Glu-Glu-Glu-Glu-Glu-Ala-Tyr-Gly-Trp-Met-Asp-Phe-Gly (SEQ ID NO: 16), preceded by the spacer -Ser-Ser-Pro-Pro-Pro-pro-Cys; (SEQ ID NO.: 7) attached to preprogastrin N-terminal of residue number 79, of the glycine-extended immunomimic of huG17. Peptide 6 (SEQ ID NO.: 6) comprises a para-nitrophenylalanine-modified, 15 amino-acid immunomimic of gly-huG17, Trp-Ile-Glu-Glu-Glu-Glu-Glu-Ala-nPhe-Gly-Trp-Met-Asp-Phe-Gly (SEQ ID NO: 17), which is preceded by the spacer -Ser-Ser-Pro-Pro-Pro-pro-Cys (SEQ ID NO.: 7) attached to preprogastrin N-terminal of residue number 79, of the glycine-extended immunomimic of huG17. Peptide 9 (SEQ ID NO.: 1) contains an amino terminal immunomimic of progastrin, -Gly-Trp-Met-Asp-Phe-Gly-Arg-Arg-Ser-Ala-Glu-Asp-Glu-Asn (SEQ ID NO: 18), preceded by the carboxy terminal spacer -Ser-Ser-pro-pro-pro-pro-Cys, (SEQ ID NO.: 8) attached to the preprogastrin N-terminal of residue 88-101 peptide, to form a human peptide mimic of progastrin.

In accordance with a preferred aspect of the invention, each of these peptides was conjugated to amino groups present on the tetanus toxoid (TT) immunogenic carrier. The linkage was via the terminal peptide cysteine residue, utilizing heterobifunctional linking agents containing a succinimidyl ester at one end and maleimide at the other end of the linking agent. To accomplish the linkage between either of the Peptides 1 and 2 above and the carrier, the cysteine of the peptide was first reduced. The dry peptide was dissolved in 0.1M sodium phosphate buffer, pH 7-9, with a 5-50 molar excess of dithiothreitol. The peptide was lyophilized and stored under vacuum until used.

The TT was activated by treatment with the heterobifunctional linking agent epsilon-maleimidocaproic acid N-hydroxysuccinimide ester (EMCS), in proportions sufficient to achieve activation of approximately 25 free amino groups per 105 molecular weight of TT.

Preparation of Purified Tetanus Toxoid: TT was purified by ultrafiltration. Final concentration of recovered purified TT was expected to be 5-40 mg/ml. The purity was determined by chromatography (SEC HPLC), protein concentration (Lowry), and free amino-groups (ninhydrin).

Peptides were obtained commercially (Biosyn Corp, USA), and reduced peptide with known purity and content was used for conjugation. Peptides were reduced with tris (2-carboxyethyl)-phosphine-HCl (TCEP), and the mixture was used in the conjugation. Ellmans assay can be used to determine free sulfhydral groups.

Activation of Tetanus Toxoid: Dilute purified TT to 5-50 mg/ml in Activation buffer. The desired amount of TT was transferred to a glass vial containing a Teflon-coated stir bar, and EMCS (50-90 mg/ml DMF) was added to the TT solution The molar ratio of EMCS/DT determines the activation level. In the final concentration step, the total volume was reduced to give >~5-50 mg TT/ml. The TT solution was determined by SEC HPLC, the protein concentration by Lowry, and the activation level by Ellman's.

Conjugation of Peptide-TT: After calculating the quantity of peptide to react with the maleimido-TT, the peptide was added to the M-TT solution. The peptide-TT conjugate was purified by ultrafiltration filtered.

The conjugates of the peptides G18 and G21 were linked to TT via EMCS and were separated from other components of the mixture by low pressure chromatography at 4° C. over a G50 Sephadex column equilibrated with 0.1-0.5M ammonium bicarbonate. In each case the conjugate was eluted in the column void volume and was lyophilized and stored, desiccated, at 4-0° C. until use.

The conjugate may be characterized as to immunomimic peptide content by a number of methods known to those skilled in the art including weight gain, amino acid analysis, etc. Conjugates of peptides G18 and G21 to TT produced by these methods were determined by amino acid analysis to have 10-30 moles of peptide per 104-106 MW of TT and all were considered suitable as immunogens for immunization of test animals. Similarly DT conjugates of G18 and G21, were prepared in the same manner to determine ELISA titers using huG17 as the substrate for assay of antibody binding.

Example 2

The peptide-TT conjugates of Example 1 were administered in emulsions of aqueous and oily phase components that were prepared as follows. The conjugate and adjuvant were dissolved in phosphate buffered saline (PBS) to produce the aqueous phase. The aqueous phase is prepared so that the concentrations of conjugate and are double the concentration that these components will have in the final emulsion. In order to prepare the immunogens used in Example 4 below, the conjugate was dissolved in PBS, pH 6.5-8.0, to a concentration of 5-12 mg/ml. (Yes it can be over this broad range, and we use it to control extent of carrier we want conjugated)

The aqueous phase was combined 1:1 (vol:vol) with the oily vehicle phase to create an emulsion that comprised the final immunogen formulation. One such vehicle is a mixture of 20-60 parts squalene, 70-30 parts squalene, 2-12 parts sorbitan monooleate, 0.6-2.0 parts aluminum monostearate, 0.1-1 parts Polysorbate 80, and 0.2-1.2 parts Polysorbate 40. The aqueous phase and oily phase vehicle can be mixed by any known method for forming a stable emulsified mixture. The emulsion must be stable upon storage, i.e., it should not undergo a significant degree of separation into aqueous and vehicle phases for a minimal storage time of several week to months. The emulsion also must be of a consistency that allows it to be injected readily through an acceptable size of hypodermic needle.

The aqueous phase containing the immunogen was emulsified 1:1 (vol:vol) with the oily vehicle mixture of the two solutions through an 18 gauge double coupled needle between two glass syringes. The mixture was pressed through the needle 50 times. The emulsified mixture then was drawn into disposable syringes for injection into animals. The final immunogen concentration in the emulsion, for in Example 4, was conjugate: hG18TT ranging in concentration from about 1 to about 5 mg per milliliter.

Example 3

The inventors constructed conjugates comprising each of the G18 and G21 peptides listed in Example 1 linked to TT and DT, as described in Examples 1 and 2. They then immunized six mice with the peptide G18 immunogen (FIGS. 1A, B) and six mice with the peptide G21 immunogen (FIGS. 1C, D).

Example 4

The inventors constructed conjugates comprising each of the G18 and G21 peptides, supra, linked to TT and DT as described in Examples 1 and 2. They then immunized four rabbits with the G18 immunogen (FIG. 2A) and four rabbits with the G21 immunogen (FIG. 2B).

The results of these ELISA tests, as presented in FIGS. 1 and 2, show that immunogens 1 and 2 (of Example 1 and 2) were effective in terms of both their potency and their eliciting of antibody in several animals species, as well as in the duration of the antibody responses induced.

Example 5

The inventors constructed conjugates comprising each of the G18 and G21 peptides linked to TT and to DT, as described above. They then immunized six mice with the G18TT immunogen and the G21TT immunogen. At peak titers (Day 42) all mice received sterile, intraperitoneal hollow fiber implants containing 50,000 human gastric cancer cells/1-2 cm tube (BCG-823) for 5 days. Hollow fiber tubules permit penetration of <500 KD molecules but not of CTL or NK cells, enabling survival of human cancer cells in immunocompetent mice. At end of 5 days each mouse had the implants removed, and the viable cells were counted by MTT assay, comparing them to control implants in non-immunized mice. As indicated, some animals also were treated with single administrations of 10 mg/kg cisplatin (CP) or 20 mg/kg 5-fluorouracil (5-FU) or a combination of 10 mg/mg each of CP+5-FU (FUP).

The results of this test are presented in FIG. 3. There is can be seen that immunogens 1 and 2 (of Example 1, and 2) were effective in terms of inhibiting the growth of human gastric cancer cells, using either of the anti-gastrin/progastrin (G18 and G21 immunogens), as well as in inducing sufficient antibody responses that were effective in the presence of conventional gastric cancer chemotherapies.

Example 6

The inventors constructed conjugates comprising each of the above-mentioned G18-a, G-18-b, G20, and G20-a peptides (SEQ ID NO.: 3-6, respectively) and compared them to G21 (SEQ ID NO.: 1). They were all linked to TT, as described in Examples 1 and 2. The inventors then immunized six mice with these immunogens (see FIGS. 4A, B, C and D) and six mice with the G21 immunogen, for comparison.

The improvements thus demonstrated arise from modifications embodied in the immunomimics and the unique spacer regions of the immunogen peptides according to the invention. The inventive peptide immunogens were tested against immunogens that did not incorporate any of the above-described immunogenic mimics and spacers, and the latter were found less effective. Accordingly, the conventional immunogens were improved by the inventors' modifying their immunomimics and/or their spacers in keeping with the invention.

---

What is claimed is:

1. A polypeptide immunogen comprising (A) a mimetic peptide comprised of (i) at least one amino acid sequence selected from the group consisting of

```
                                            (SEQ ID NO.: 1)
Cys-pro-Pro-Pro-Pro-Ser-Ser-Gly-Trp-Asp-nPhe-
Gly-Arg-Arg-Ser-Ala-Glu-Asp-Glu-Asn, (SEQ ID NO.: 2)
pGlu-Gly-Pro-Trp-β-isoVal-Glu-Glu-Glu-Glu-Glu-
Ala-Ser-Ser-Pro-Pro-Pro-pro-Cys, (SEQ ID NO.: 3)
pGlu-Gly-Pro-Trp-Ile-Glu-Glu-Glu-Glu-Glu-Ala-
Ser-Ser-Pro-Pro-Pro-pro-Cys, (SEQ ID NO.: 4)
pGlu-Gly-Pro-Trp-Val-Glu-Glu-Glu-Glu-Glu-Ala-
Ser-Ser-Pro-Pro-Pro-pro-Cys, (SEQ ID NO.: 5)
Cys-pro-Pro-Pro-Pro-Trp-Leu-Glu-Glu-Glu-
Glu-Ala-Tyr-Gly-Trp-Met-Asp-Phe-Gly,
and (SEQ ID NO.: 6)
Cys-pro-Pro-Pro-Pro-Trp-Leu-Glu-Glu-Glu-
Glu-Ala-nPhe-Gly-Trp-Met-Asp-Phe-Gly
``` joined to (ii) a 7 amino-acid spacer and (B) an immunogenic carrier coupled to said mimetic peptide.

2. The polypeptide immunogen according to claim 1, wherein the mimetic peptide comprises the amino acid sequence:
Cys-pro-Pro-Pro-Pro-Ser-Ser-Gly-Trp-Asp-nPhe-Gly-Arg-Arg-Ser-Ala-Glu-Asp-Glu-Asn (SEQ ID NO.: 1).

3. The polypeptide immunogen composition according to claim 1, wherein the immunogenic carrier is selected from the group consisting of tetanus toxoid, diphtheria toxoid, pertussin toxoid, and tuberculin pure protein derivative.

4. The polypeptide immunogenic composition according to claim 3, wherein the immunogenic carrier is tetanus toxoid.

5. An immunogenic composition comprising an immunization-effective amount of the polypeptide immunogen according to claim 1 and a pharmaceutically acceptable vehicle for said immunogen.

6. The immunogenic composition according to claim 5, wherein said pharmaceutically acceptable carrier comprises an emulsion of an aqueous phase, in which said immunogen is present, and an oily phase.

7. The immunogenic composition according to claim 6, wherein said oily phase comprises at least one selected from the group consisting of squalene, squalane, sorbitan monooleate, Polysorbate 40, and Polysorbate 80.

8. The immunogenic composition according to claim 6, wherein said oily phase comprises an emulsifier.

9. The immunogenic composition according to claim 6, wherein either said oily phase or said aqueous phase contains at least one adjuvant.

10. The immunogenic composition according to claim 9, wherein said adjuvant is selected from the group consisting of Nor-MDP, imiquimod, cyclic diguanylate, threonyl-N-acetyl-muramyl-L-alanyl-D-isoglutamine, Isoprinosine, trehalose dimycolate, QS-21, alpha-galactosylceramide, and alpha-glucosylceramide.

11. The immunogenic composition according to claim 9, wherein said adjuvant is selected from the group consisting of Ergamisol, Cimetidine, Praziquantel, uric acid, mannan and derivatives of mannan, and vitamin E.

12. A spacer peptide selected from the group consisting of:

```
                                            (SEQ ID NO.: 7)
Ser-Ser-Pro-Pro-Pro-pro-Cys;

(SEQ ID NO.: 8)
Ser-Ser-pro-pro-pro-pro-Cys;

(SEQ ID NO.: 9)
Thr-Thr-Pro-Pro-Pro-pro-Cys;
and (SEQ ID NO.: 10)
Thr-Thr-pro-pro-pro-pro-Cys.
```

13. The polypeptide immunogen composition according to claim 1, wherein the mimetic peptide comprises the amino acid sequence:
pGlu-Gly-Pro-Trp-Ile-Glu-Glu-Glu-Glu-Glu-Ala-Ser-Ser-Pro-Pro-Pro-pro-Cys (SEQ ID NO.: 3).

* * * * *

SEQUENCE LISTING

```
<160> NUMBER OF SEQ ID NOS: 18

<210> SEQ ID NO 1
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Pro
<220> FEATURE:
<221> NAME/KEY: MOD_RES
<222> LOCATION: (12)..(12)
<223> OTHER INFORMATION: nPhe

<400> SEQUENCE: 1

Cys Pro Pro Pro Pro Ser Ser Gly Trp Met Asp Phe Gly Arg Arg Ser
1               5                   10                  15

Ala Glu Asp Glu Asn
            20

<210> SEQ ID NO 2
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pGlu
<220> FEATURE:
<221> NAME/KEY: MOD_RES
<222> LOCATION: (5)..(5)
<223> OTHER INFORMATION: Beta-isoVal
<220> FEATURE:
<221> NAME/KEY: MOD_RES
<222> LOCATION: (17)..(17)
<223> OTHER INFORMATION: D-Pro

<400> SEQUENCE: 2

Glu Gly Pro Trp Val Glu Glu Glu Glu Ala Ser Ser Pro Pro Pro
1               5                   10                  15

Pro Cys

<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pGlu
<220> FEATURE:
<221> NAME/KEY: MOD_RES
```

-continued

```
<222> LOCATION: (17)..(17)
<223> OTHER INFORMATION: D-Pro

<400> SEQUENCE: 3

Glu Gly Pro Trp Ile Glu Glu Glu Glu Ala Ser Ser Pro Pro Pro
1               5                   10                  15

Pro Cys

<210> SEQ ID NO 4
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pGlu
<220> FEATURE:
<221> NAME/KEY: MOD_RES
<222> LOCATION: (17)..(17)
<223> OTHER INFORMATION: D-Pro

<400> SEQUENCE: 4

Glu Gly Pro Trp Val Glu Glu Glu Glu Ala Ser Ser Pro Pro Pro
1               5                   10                  15

Pro Cys

<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Pro

<400> SEQUENCE: 5

Cys Pro Pro Pro Pro Trp Leu Glu Glu Glu Glu Ala Tyr Gly Trp
1               5                   10                  15

Met Asp Phe Gly
            20

<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Pro
<220> FEATURE:
<221> NAME/KEY: MOD_RES
<222> LOCATION: (14)..(14)
<223> OTHER INFORMATION: nPhe

<400> SEQUENCE: 6

Cys Pro Pro Pro Pro Trp Leu Glu Glu Glu Glu Ala Phe Gly Trp
1               5                   10                  15

Met Asp Phe Gly
            20
```

```
<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: D-Pro

<400> SEQUENCE: 7

Ser Ser Pro Pro Pro Pro Cys
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(6)
<223> OTHER INFORMATION: D-Pro

<400> SEQUENCE: 8

Ser Ser Pro Pro Pro Pro Cys
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: D-Pro

<400> SEQUENCE: 9

Thr Thr Pro Pro Pro Pro Cys
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(6)
<223> OTHER INFORMATION: D-Pro

<400> SEQUENCE: 10

Thr Thr Pro Pro Pro Pro Cys
1               5

<210> SEQ ID NO 11
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: pGlu
<220> FEATURE:
<221> NAME/KEY: MOD_RES
<222> LOCATION: (5)..(5)
<223> OTHER INFORMATION: IsoVal
<220> FEATURE:
<221> NAME/KEY: MOD_RES
<222> LOCATION: (17)..(17)
<223> OTHER INFORMATION: D-Pro

<400> SEQUENCE: 11

Glu Gly Pro Trp Val Glu Glu Glu Glu Ala Ser Ser Pro Pro Pro
1               5                   10                  15

Pro Cys

<210> SEQ ID NO 12
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pGlu
<220> FEATURE:
<221> NAME/KEY: MOD_RES
<222> LOCATION: (17)..(17)
<223> OTHER INFORMATION: D-Pro

<400> SEQUENCE: 12

Glu Gly Pro Trp Val Glu Glu Glu Glu Ala Thr Thr Pro Pro Pro
1               5                   10                  15

Pro Cys

<210> SEQ ID NO 13
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: nPhe

<400> SEQUENCE: 13

Gly Trp Met Asp Phe Gly Arg Arg Ser Ala Glu Asp Glu Asn
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pGlu
<220> FEATURE:
<221> NAME/KEY: MOD_RES
```

```
<222> LOCATION: (6)..(6)
<223> OTHER INFORMATION: IsoVal

<400> SEQUENCE: 14

Glu Gly Pro Trp Leu Val Glu Glu Glu Glu Ala
1               5                   10

<210> SEQ ID NO 15
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pGlu

<400> SEQUENCE: 15

Glu Gly Pro Trp Ile Glu Glu Glu Glu Ala Tyr Gly Trp Met Asp
1               5                   10                  15

Phe Gly

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Trp Ile Glu Glu Glu Glu Glu Ala Tyr Gly Trp Met Asp Phe Gly
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: nPhe

<400> SEQUENCE: 17

Trp Ile Glu Glu Glu Glu Ala Phe Gly Trp Met Asp Phe Gly
1               5                   10                  15

<210> SEQ ID NO 18
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Trp Met Asp Phe Gly Arg Arg Ser Ala Glu Asp Glu Asn
1               5                   10
```